United States Patent [19]
Gross et al.

[11] Patent Number: 5,356,632
[45] Date of Patent: Oct. 18, 1994

[54] TRANSDERMAL DRUG DELIVERY DEVICE

[75] Inventors: Joseph Gross, Moshav Mazor; Shlomo Zucker, Michmoret, both of Israel

[73] Assignee: S.I. Scientific Innovations Ltd., Petach Tikva, Israel

[21] Appl. No.: 759,006

[22] Filed: Sep. 12, 1991

[51] Int. Cl.⁵ .............................................. A61F 13/00
[52] U.S. Cl. ..................... 424/449; 424/448; 602/64; 604/20
[58] Field of Search ............................. 424/449; 604/20

[56] References Cited

U.S. PATENT DOCUMENTS

| | | | |
|---|---|---|---|
| 4,474,570 | 10/1984 | Ariura et al. | 128/798 |
| 4,486,194 | 12/1984 | Ferrara | 424/449 |
| 4,585,652 | 4/1986 | Miller et al. | 424/449 |
| 4,640,689 | 2/1987 | Sibalis | 604/20 |
| 4,708,716 | 11/1987 | Sibalis | 424/449 |
| 4,722,726 | 2/1988 | Sanderson et al. | 604/20 |
| 4,878,892 | 11/1989 | Sibalis et al. | 604/20 |
| 4,931,046 | 6/1990 | Newman | 128/803 |
| 4,940,456 | 7/1990 | Sibalis | 604/20 |
| 4,942,883 | 7/1990 | Newman | 424/449 |
| 5,002,527 | 3/1991 | Reller et al. | 604/20 |
| 5,006,108 | 4/1991 | La Prade | 128/803 |
| 5,023,085 | 6/1991 | Francoeur et al. | 424/449 |
| 5,042,975 | 8/1991 | Chien et al. | 604/20 |
| 5,080,646 | 1/1992 | Theeuwes et al. | 604/20 |
| 5,135,480 | 8/1992 | Bannon | 604/20 |

FOREIGN PATENT DOCUMENTS

| | | | |
|---|---|---|---|
| 0371342 | 6/1983 | Austria | . |
| 0417290 | 3/1991 | European Pat. Off. | . |

*Primary Examiner*—Phelan, D. Gabrielle
*Attorney, Agent, or Firm*—Benjamin J. Barish

[57] ABSTRACT

A transdermal drug delivery device includes anode and cathode electrodes supported on a base member in spaced relation to each other to define a gap therebetween, a gel containing a liquid drug to be delivered covering the gap and in contact with both of the electrodes, and a liquid permeable sheet covering the gel containing the liquid to be delivered.

20 Claims, 2 Drawing Sheets

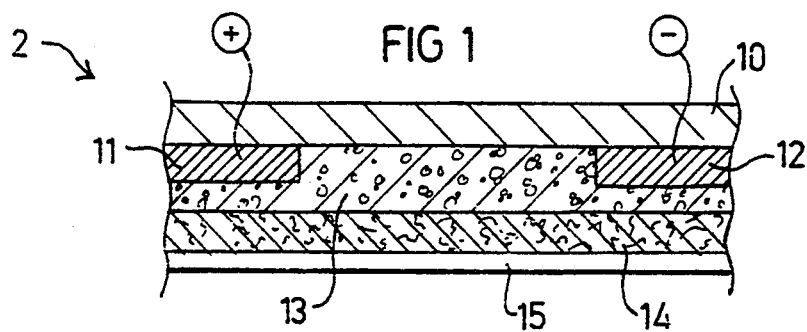
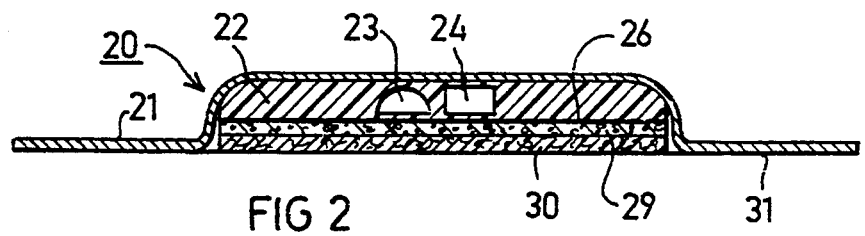
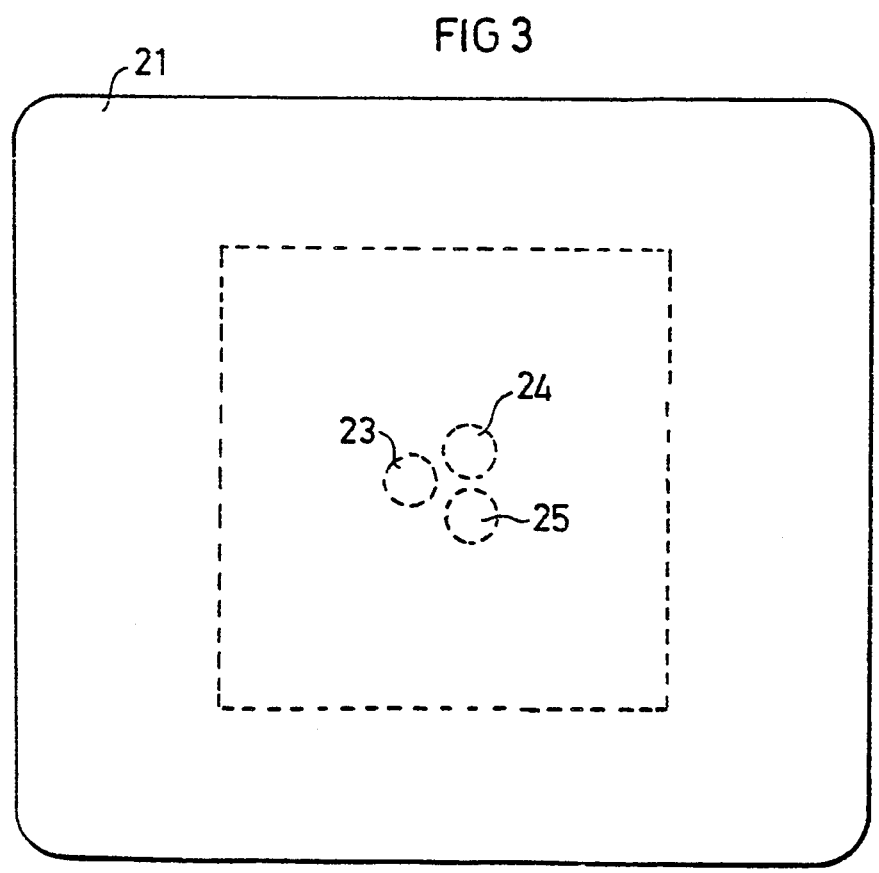

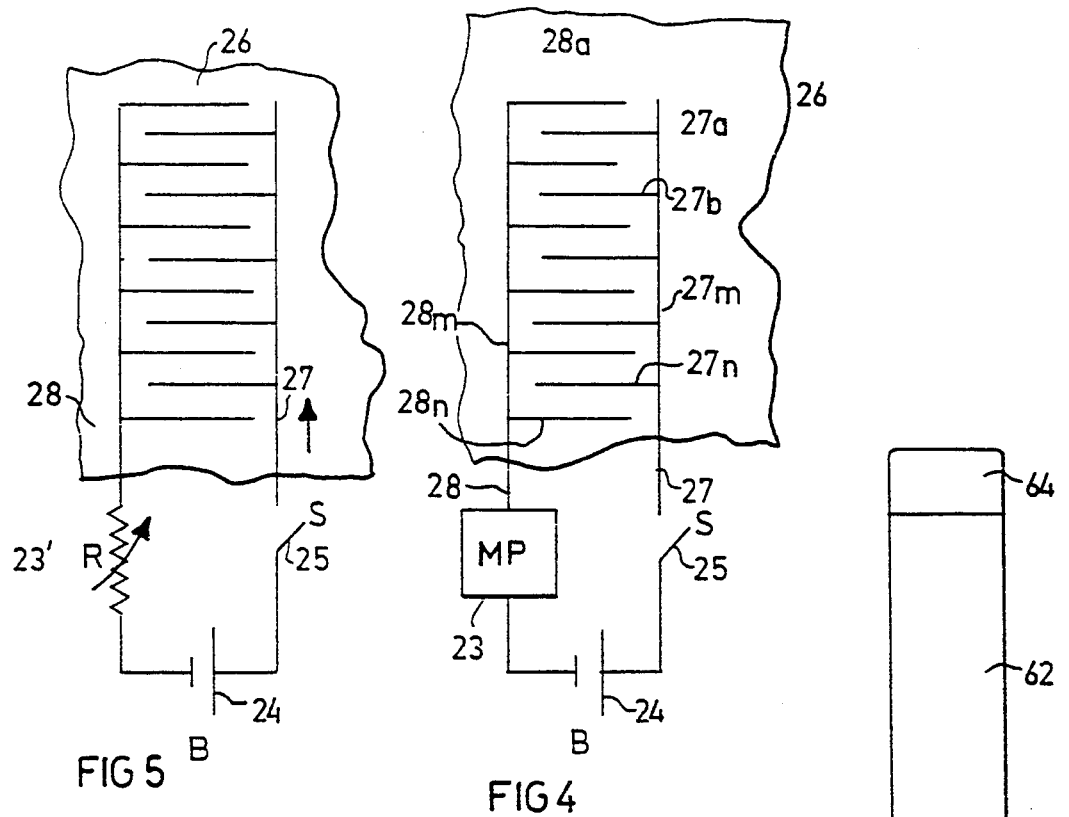
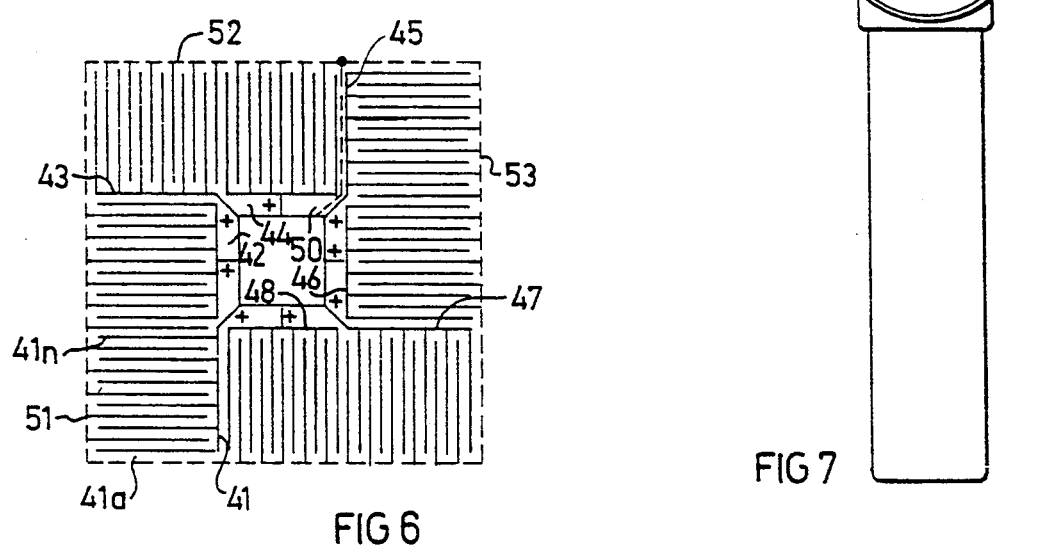

TRANSDERMAL DRUG DELIVERY DEVICE

FIELD AND BACKGROUND OF THE INVENTION

The present invention relates to a device for the transdermal delivery of a drug.

The transdermal delivery of a drug is frequently done by a "passive patch" or an "active patch" applied to the skin of the patient. A passive patch employs chemical potential as the driving force to deliver the drug, whereas an active patch employs an electrical potential as the driving force to deliver the drug.

Various types of active patches have been described in the literature based on iontophoresis (or electrophoresis or electroosmosis), wherein ionic (charged) molecules of the drug are delivered to the skin tissue of the patient by the passage of electric current through an electrolyte solution containing the drug. In such a technique, the drug to be delivered is contacted by only one of the electrodes. Thus, contacting the drug by the anode electrode produces positive ions which are driven into the skin at the anode, and contacting the drug with the cathode electrode produces ions with negative charges which are driven into the cathode. A review of this technique appears in the article titled "Iontophoretic Delivery of Drugs: Fundamentals, Developments and Biomedical Applications" by Ajay K. Banga and Yie W. Chien, Journal of Controlled Release, 7 (1988) 1-24.

The main drawback in the iontophoresis delivery of a drug is the danger of electric shock, skin irritation or burns, since the electrodes are in direct contact with the patient's skin. Thus, the rate of delivery of the drug to the skin is generally linearly proportional to the density of the electrical current supplied, but the power required, or heat generated, is generally proportional to the square of the electrical current supplied.

OBJECTS AND BRIEF SUMMARY OF THE INVENTION

An object of the present invention is to provide a new transdermal drug delivery device for delivering a liquid drug to a patient.

According to the present invention, there is provided a transdermal drug delivery device, for application to a subject's skin, comprising: a base member of insulating material; an anode electrode and a cathode electrode supported on said base member in spaced relation to each other to define a gap therebetween; means for connecting the electrodes to a voltage source; and an insulating layer releasably containing a liquid drug to be delivered covering said gap and both of said electrodes, such that neither of said electrodes comes into contact with the subject's skin when applied thereto. Preferably, and in accordance with the described preferred embodiments, the insulating layer is a gel releasably containing the liquid drug to be delivered, and is in contact with both of the electrodes.

It is to be particularly noted that in the above described device, both electrodes contact the gel containing the drug to be delivered and neither electrode contacts the patient's skin. This is to be distinguished from the iontophoresis technique for transdermal drug delivery wherein only one of the electrodes contacts the drug-containing medium and both electrodes contact the subject's skin. Accordingly, the transdermal drug delivery device constructed in accordance with the present invention provides the "control" advantage of the active patch, but not the disadvantage of the danger of electric shock, skin irritation or burns. The novel transdermal drug delivery device may therefore be called a "controlled passive patch" device.

It has been found that the novel device causes the gel to release the liquid drug at a rate having a very close linear relation to the magnitude of the current supplied, i.e., the density of the current flowing through the gel. Thus, if the current is doubled, the rate of release of the liquid drug from the gel is approximately doubled. Therefore close linear control may be provided of the drug delivery rate.

Particularly good results have been obtained when the outer face of the gel is covered by a liquid permeable sheet, preferably a porous absorbent sheet of hydrophylic material, such as porous absorbent paper.

According to further features in the described preferred embodiments, the base member further supports a battery having its positive-terminal connected to the anode electrode, and its negative-terminal connected to the cathode electrode for supplying current to the gel in contact with the electrodes. In the described preferred embodiments, the backing sheet further supports electrical control means for controlling the current supplied to the gel. Preferably, the electrical control means includes a pre-programmable mircroprocessor for pre-programming the magnitude of the current to be supplied to the gel, and the time periods during which the electrical current is to be supplied to the gel.

According to further features in the described preferred embodiments, each of the electrodes includes a plurality of branches electrically connected together but physically spaced from each other. The branches of the anode electrode are paired with, but spaced from, the branches of the cathode electrode to form a plurality of gaps, all of which gaps are covered by the gel containing the liquid drug to be delivered.

More particularly, in the described embodiments, the electrode branches are in the form of parallel strips, the strips of the anode electrode branches alternating with the strips of the cathode electrode branches. According to one preferred embodiment, the electrodes are arranged in a plurality of groups occupying different areas of the base sheet, enabling the electrodes of each group to be selectively energized at different times to deliver the drug of the gel in the respective area at different times.

Further features and advantages of the invention will be apparent from the description below.

BRIEF DESCRIPTION OF THE DRAWINGS

The invention is herein described, by way of example only, with reference to the accompanying drawings, wherein:

FIG. 1 is a diagram illustrating one form of transdermal drug delivery device constructed in accordance with the present invention;

FIG. 2 illustrates another form of transdermal drug delivery device constructed in accordance with the present invention;

FIG. 3 is a plan view of the device illustrated in FIG. 2;

FIGS. 4 and 5 schematically illustrate an electrode array and two types of controls for a transdermal drug delivery device constructed according to FIGS. 2 and 3;

FIG. 6 illustrates the electrode array of a further form of transdermal drug delivery device constructed in accordance with the present invention; and FIG. 7 illustrates the device of FIG. 6 as embodied in a wrist band for application to the wrist of a patient.

DESCRIPTION OF PREFERRED EMBODIMENTS

The transdermal drug delivery device illustrated in FIG. 1, therein designated 2, comprises a base member 10 of insulating material, such as a plastic sheet. An anode electrode 11 and a cathode electrode 12 are applied to one face of base member 10 in spaced relation to each other so as to define a gap between the two electrodes. A layer of gel 13, containing the liquid drug to be delivered, is applied over the two electrodes 11, 12, so as to be in direct contact with both electrodes and also to fill the gap 13 between both electrodes. The opposite face of the gel layer 13, i.e., opposite to that facing the base sheet 10, is covered by a hydrophylic liquid-permeable sheet 14, preferably a sheet of porous absorbent paper. The device is to be applied with sheet 14 in direct contact with the skin 15 of the patient to receive the drug transdermally.

It has been found that when the anode 11 and cathode 12 are connected to a source of electrical current, e.g., via their respective terminals schematically indicated at 16 and 17, respectively, the liquid drug contained within the gel layer 13 is released from the gel at a rate which depends generally linearly on the magnitude of the electrical current through the gel layer. This liquid drug is absorbed by the sheet 14 and is delivered to the patient's skin 15. Thus, by controlling the magnitude of electrical current applied to the two electrodes 11, 12, the rate of release of the drug from the gel 13 to the porous paper sheet 14, and thereby the rate of delivery of the drug to the patient's skin 15, can be controlled.

As one example, the gel could be a hydrogel, and the liquid drug to be delivered could be nitroglycerine. It was found that in such a gel-drug mixture, applying one milliamp of electric current between the two electrodes released the drug from the gel at a rate of 0.01 cc/min, whereas when the electric current was increased to 10 milliamps, the rate of release was correspondingly increased to about 0.10 cc/min.

In addition to nitroglycerine, other drugs may be delivered in this manner, such as a beta-blocker, analgesics, and many of the other drugs mentioned in the above-cited review by Ajay J. Banga and Yie W. Chien.

FIGS. 2 and 3 illustrate a transdermal drug delivery device embodied in the form of a patch that may be adhesively applied to the patient's skin. The device, generally designated 20 in FIGS. 2 and 3, comprises a body member including base sheet 21, e.g., of flexible plastic material, and a layer 22 of resilient plastic material bonded to the inner face of sheet 21. Layer 22, e.g., of sponged plastic material, embeds a microprocessor 23, a battery 24, and an electrical switch 25, for supplying power to the device. A printed circuit film 26 is bonded to the outer face of layer 22. The outer face of the printed circuit film 26 carries an array of electrically-conductive pathways, as more particularly illustrated in FIG. 4, which pathways constitute an anode electrode 27 and a cathode electrode 28.

A layer of a gel 29, containing the liquid drug to be delivered by the device, is applied to the outer surface of the printed circuit film 26 to cover, and to be in good contact with, the two electrodes 27 and 28. A sheet of a hydrophylic liquid-permeable material 30, such as porous absorbent paper, is applied to the outer face of the gel layer 29. A peelable protective film 31 covers the outer face of the liquid-permeable sheet 30 and the inner face of the base film 21, and is removably retained in place by adhesive on the underface of the base sheet.

As shown in FIG. 4, each of the two electrodes 27, 28 includes a plurality of branches electrically connected together but physically spaced from each other, with the branches of one electrode being paired with, but spaced from, the branches of the other electrode to form a plurality of gaps all of which are covered by the gel layer 29. Thus, the anode electrode 27 includes a plurality of branches 27a–27n in the form of parallel, spaced strips of conductive material; and similarly the cathode electrode 28 includes a plurality of branches 28a–28n also in the form of parallel, spaced strips alternating with the strips 27a–27n of the anode electrode. A plurality of parallel gaps are thus formed between the anode electrode sections 27a–27n, and the respective cathode electrode sections 28a–28n.

The gel layer 29 covers these parallel gaps and is in good contact with all the above branches of the anode and cathode electrodes. When battery 24 is connected by switch 25 to the two electrodes 27, 28, an electrical current, under the control of microprocessor 23, thus flows through the gel bridging the gaps between each pair of these electrode branches. As described above, the gel layer 29 releases the liquid drug contained in the layer at a rate substantially linearly to the density of the current through the gel. The released drug is absorbed by the porous paper sheet 30 in contact with the patient's skin and is thereby applied to the patient's skin at a rate corresponding to the density of the current passing through the gel layer.

Microprocessor 23 may be pre-programmed to control the magnitude (or density) of the electrical current supplied to the two electrodes 27, 28, and thereby the rate, as well as the time, of delivery of the liquid drug from the gel layer 29.

FIG. 5 illustrates a variation in the construction of the device, in that instead of including a microprocessor 23, there is included merely a presettable resistor 23' to control the magnitude of the electrical current applied to the electrodes, and thereby the rate of delivery of the drug. The construction and mode of operation of the device illustrated in FIG. 5 are otherwise the same as that described above with respect to FIG. 4.

In the device of FIGS. 2–5, the electrical switch 25 may have an operator (not shown) which is exposed on the outer face of the base sheet 21, so that the electrical switch can be closed after the patch has been applied. Alternatively, the electrical switch 25 can be included in the microprocessor 23 and conveniently actuated in any suitable manner, i.e., when the protective film 31 is stripped from the adhesively-coated base sheet 21 at the time the device is applied to the patient's skin.

FIG. 6 illustrates a device which may be similar to that described above with respect to FIGS. 2–5, except for the construction and disposition of the two electrodes on the printed circuit film 26. Thus, in the construction illustrated in FIG. 6, the two electrodes are arranged in a plurality of groups occupying different areas of the printed circuit film (26), and thereby of the base sheet 21. This enables the electrodes of each group to be selectively energized at different times (and also with different current magnitudes) for purposes of dispensing the drug of the gel layer (29, FIG. 2) in the respective area at different times (and at different rates, if desired).

Thus, as shown in FIG. 6, the anode is constituted of an array, generally designated 40, constituted of a plurality of separate anode electrodes 41-48, with each anode electrode including a plurality of branches 41a-41n, 42a-42n, etc., in parallel spaced relation to each other. The cathode electrode, generally designated 50, is similarly formed of a plurality of electrodes 51-58 but, in this case, all electrically connected together. Each cathode electrode 51-58 includes a plurality of straight branches 51a-51n, 52a-52n, etc., also in parallel spaced relation to each other, but in staggered relation with respect to the branches of the anode electrode.

The anode electrode sections and cathode electrode branches thus define eight groups of anode-cathode electrodes in eight different areas of the device. All of these electrodes are covered by the gel layer (29, FIG. 2) containing the drug to be delivered. Only one of the eight groups of electrodes may be energized at any one time so as to cause only that portion of the device to deliver the drug, all under the control of the microprocessor (23, FIG. 4). The microprocessor 23 may be pre-programmed so as to energize only one of the eight groups of electrodes each predetermined time period, according to the particular drug delivery regimen.

FIG. 2 illustrates the drug delivery device applied in the form of a patch adhesively bonded to the skin of the patient. FIG. 7 illustrates a variation, wherein the drug delivery device, therein designated 60, is applied in the form of a wrist band to the wrist of a patient. Thus, the device illustrated in FIG. 7 includes a strap 62 and a buckle 64 for applying the device to the patient's wrist. The drug delivery device 60 in the FIG. 7 embodiment may otherwise be the same as described with respect to FIGS. 1-6.

While the invention has been described with respect to several preferred embodiments, it will be appreciated that many other variations, modifications and applications of the invention may be made.

What is claimed is:

1. A transdermal drug delivery device for application to a subject's skin, comprising:
   a base member of insulating material;
   an anode electrode and a cathode electrode supported on said base member in spaced relation to each other to define a gap therebetween;
   means for connecting said electrodes to a voltage source;
   and an insulating layer releasably containing a liquid drug to be delivered covering said gap and both of said electrodes such that neither of said electrodes comes into contact with the subject's skin when applied thereto.

2. The device according to claim 1, further including a liquid permeable sheet covering said insulating layer releasably containing the liquid to be delivered.

3. The device according to claim 2, wherein said liquid permeable sheet is a porous absorbent sheet of hydrophilic material.

4. The device according to claim 2, wherein said base member includes a backing sheet having an adhesive coating for adhesively applying the device to a patient's skin with the liquid permeable sheet in contact with the patient's skin.

5. The device according to claim 2, further including a wrist band for applying the device to the wrist of a patient, with the liquid-permeable sheet in contact with the patient's skin.

6. The device according to claim 1, wherein said base member further supports a battery having its positive-terminal connected to said anode electrode, and its negative-terminal connected to said cathode electrode for supplying current to said insulating layer via said electrodes.

7. The device according to claim 6, wherein said base member further supports an electrical control means for controlling the current supplied to said insulating layer.

8. The device according to claim 7, wherein said electrical control means comprises a presettable resistor for presetting the magnitude of the current to be supplied to said insulating layer, and an electrical switch for supplying the electrical current to said insulating layer.

9. The device according to claim 7, wherein said electrical control means comprises a preprogrammable microprocessor for pre-programming the magnitude of the current to be supplied to said insulating layer, and the time periods during which the electrical current is to be supplied to the insulating layer.

10. The device according to claim 1, wherein each of said electrodes includes a plurality of branches electrically connected together but physically spaced from each other, the branches of the anode electrode being paired with, but spaced from, the branches of the cathode electrode to form a plurality of gaps, all of which gaps are covered by said insulating layer releasably containing the liquid drug to be delivered.

11. The device according to claim 10, wherein said electrode branches are in the form of parallel strips, the strips of the anode electrode branches alternating with the strips of the cathode electrode branches.

12. The device according to claim 11, wherein said electrodes are arranged in a plurality of groups occupying different areas of said base sheet, enabling the electrodes of each group to be selectively energized at different times to deliver the drug of the insulating layer in the respective area at different times.

13. A transdermal drug delivery device for application to a subject's skin, comprising:
   a base member of insulating material;
   an anode electrode and a cathode electrode supported on said base member in spaced relation to each other to define a gap therebetween;
   an insulating layer including a gel containing a liquid drug to be delivered covering said gap and in contact with and covering both of said electrodes;
   means for connecting said electrodes to a voltage source;
   and a liquid permeable sheet covering said gel containing the liquid to be delivered such that neither of said electrodes comes into contact with the subject's skin when applied thereto.

14. The device according to claim 13, wherein said liquid permeable sheet is a porous absorbent sheet of hydrophilic material.

15. The device according to claim 13, wherein said base member further supports a battery having its positive-terminal connected to said anode electrode, and its negative-terminal connected to said cathode electrode for supplying current to said gel in contact with said electrodes.

16. The device according to claim 13, wherein said base member further supports an electrical control mean for controlling the current supplied to said gel.

17. The device according to claim 16, wherein said electrical control means comprises a preprogrammable microprocessor for pre-programming the magnitude of the current to be supplied to said gel, and the time periods during which the electrical current is to be supplied to the gel.

18. The device according to claim 13, wherein each of said electrodes includes a plurality of branches electrically connected together but physically spaced from each other, the branches of the anode electrode being paired with, but spaced from, the branches of the cathode electrode to form a plurality of gaps, all of which gaps are covered by said gel containing the liquid drug to be delivered.

19. The device according to claim 18, wherein said electrode branches are in the form of parallel strips, the strips of the anode electrode branches alternating with the strips of the cathode electrode branches.

20. The device according to claim 19, wherein said electrodes are arranged in a plurality of groups occupying different areas of said base sheet, enabling the electrodes of each group to be selectively energized at different times to deliver the drug of the gel in the respective area at different times.

* * * * *